(12) United States Patent
Kostylev et al.

(10) Patent No.: US 6,273,860 B1
(45) Date of Patent: Aug. 14, 2001

(54) BIOPSY APPARATUS

(75) Inventors: Alexander N. Kostylev; Constantine V. Novikov, both of St. Petersburg (RU); Leon L. Pesotchinsky, Los Altos Hills, CA (US)

(73) Assignee: LSVP International, Inc., Los Altos, CA (US)

( * ) Notice: Subject to any disclaimer, the term of this patent is extended or adjusted under 35 U.S.C. 154(b) by 0 days.

(21) Appl. No.: 09/305,687

(22) Filed: May 4, 1999

Related U.S. Application Data
(60) Provisional application No. 60/084,019, filed on May 4, 1998.

(51) Int. Cl.⁷ .................................................. A61B 10/00
(52) U.S. Cl. .............................................................. 600/564
(58) Field of Search ................................... 600/564, 562, 600/563, 565, 566; 606/127, 170

(56) References Cited

U.S. PATENT DOCUMENTS

| | | | |
|---|---|---|---|
| 4,815,476 | 3/1989 | Clossick | 128/751 |
| 4,817,630 | 4/1989 | Schintgen et al. | 128/751 |
| 4,887,612 | 12/1989 | Esser et al. | 128/751 |
| 5,097,728 | 3/1992 | Cox et al. | 76/119 |
| 5,373,854 | 12/1994 | Kolozsi | 128/749 |
| 5,419,220 | 5/1995 | Cox | 76/104.1 |
| 5,507,296 * | 4/1996 | Bales et al. | 600/564 |
| 5,535,754 | 7/1996 | Doherty | 128/751 |
| 5,897,507 * | 4/1999 | Kortenbach et al. | 600/562 |

* cited by examiner

*Primary Examiner*—Eric F. Winakur
*Assistant Examiner*—Brian Szmal
(74) *Attorney, Agent, or Firm*—Carol D. Titus; James J. Leary

(57) ABSTRACT

An endoscopic instrument having one or two moving jaws. One or two control wires attach to the lower portion of the moving jaws. Each control wire is located within a groove or enclosed channel which passes along the side and preferably to the back of the jaw. The end of the control wire is connected with the jaw so that when the control wire is moved, the force from the wire moved the jaw about its pivot point. If two moving jaws are present, the pivot point is preferably centrally located in the housing. If only a single moving jaw is used, the pivot point may be central, or it may be offset.

24 Claims, 4 Drawing Sheets

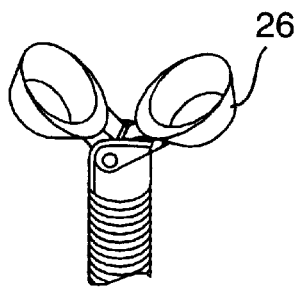
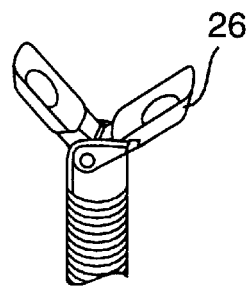
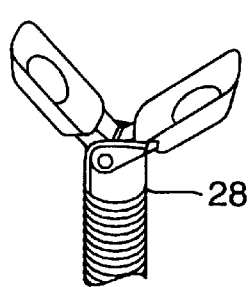
FIG. 6        FIG. 7        FIG. 8
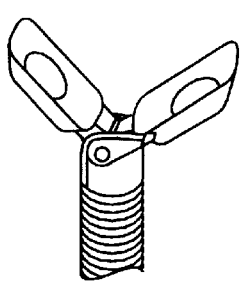
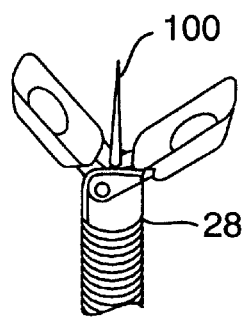
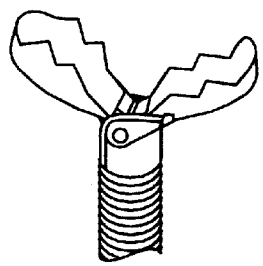
FIG. 9        FIG. 10        FIG. 11
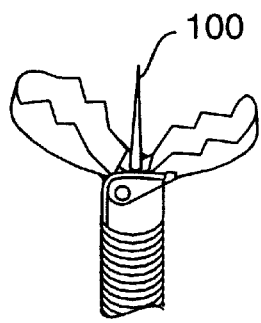
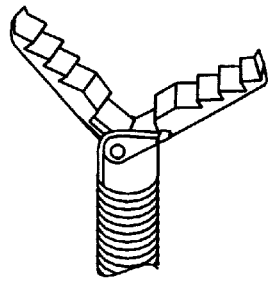
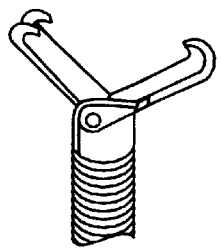
FIG. 12        FIG. 13        FIG. 14

BIOPSY APPARATUS

CROSS REFERENCE TO OTHER APPLICATIONS

This application claims the benefit of US Provisional Patent Application Number 60/084,019, filed May 4, 1998, which is hereby incorporated by reference in its entirety.

FIELD OF THE INVENTION

The present invention relates to medical instruments. More particularly, it relates to an endoscopic instrument that may be used as biopsy forceps, graspers, etc.

BACKGROUND OF THE INVENTION

Over time, a variety of endoscopic biopsy forceps, graspers, and other related apparatuses have been developed to take samples of tissue or grasp and remove material during endoscopic procedures. Normally, the forceps, which are adapted to cut and remove body tissue for examination, are inserted together with an endoscope deep into a body cavity being examined. The forceps conventionally used in such procedures utilize complex arrangements of linkage assemblies or cam type devices for articulating the jaws of the forceps. As such instruments are of small size, such complexity results in complex machining and manufacturing procedures which greatly increase the cost of such instruments. The multiple connections also increase the amount of play, which may increase the distortion of the movement of the jaws of the device. Thus, present biopsy devices are generally very expensive and, the jaw actuating mechanisms are complex and may be inaccurate.

The small size and number of the linkages and hinge pins also decrease the durability of the biopsy forceps and make them vulnerably to breakage. This is an important consideration, especially when working within a patient where retrieval of a dissociated part may be difficult or dangerous to the patient. Large numbers of small linkages and hinges-also increase the cost and difficulty of manufacturing and assembly.

The combination of jaws, linkages, and outer housing results in an instrument jaw/housing assembly having a significant rigid length. This rigidity associated with the instrument increases the difficulty of navigation through the bent channel of the endoscope, as well as increasing the potential for damage of the endoscope instrument channel through which the device is passed to obtain a tissue sample. A single endoscope may be used for many endoscopic procedures, and, in some cases an endoscopic biopsy procedure requires multiple insertions and removals of the device. Each insertion or removal of the biopsy instrument through the narrow channel in the endoscope can cause potential damage to the channel of the endoscope or to the biopsy instrument itself. This is especially problematic in cases where a tortuous passage leads to the cavity from which the sample is obtained.

Further damage to the endoscope instrument channel may be caused by a link or a member of the forceps which protrudes from the perimeter of the rest of the forceps. This problem may arise if the forceps are unable to close completely or if a portion of the mechanism jams, or even if the mechanism merely has excess play. When the forceps are inserted or removed from the endoscope under these conditions, the exposed link or member may scrape, scratch or otherwise damage the channel.

Since many current biopsy devices are intended for multiple use, damage to the endoscope or biopsy device itself is even less desirable. Furthermore, in conventional biopsy forceps, the intended multiple use of the instrument requires extensive cleaning and sterilizing procedures to be performed to comply with medical standards and use of the instruments. When used multiple times, a biopsy instrument must be sterilized between uses by immersing a contaminated instrument in a suitable chemical sterilizing solution, subjecting the apparatus to sterilization in an autoclave, or some other sterilization procedure. The sterilization and cleaning procedures will often decrease the performance or useful life span of the instrument, thereby magnifying the problem created by the complexity of manufacture and many parts which quickly wear. Further, some devices which are intended only for single use still incorporate complex linkage or cam type devices for proper movement of the biopsy jaws. This greatly inhibits their use as the costs associated with such instruments are normally still very high.

Other deficiencies of the prior art endoscopic biopsy forceps are found in activation of the biopsy jaws for opening and closing of the jaws. The complexity and many moving parts of prior art devices cause the jaws to misalign when the jaws are actuated. This is also a problem with devices which utilize a living hinge. A living hinge operates by using the flexibility and deformation of the material of the hinge to allow the jaws to move. However, the same flexibility allows the jaws to twist which means that the cutting edges of the jaws may not meet properly and the sample is not removed cleanly from the rest of the organ. In extreme cases, the forceps may fail entirely and require that a new instrument be used and/or a lost piece of the instrument be retrieved from the patient.

Due to their geometry, many prior art devices provide the greatest amount of force from control wire to the jaws when the jaws are in their fully open position, and the least amount of force when the jaws are in their fully closed position. In use, these characteristics are the opposite of what is most efficient and useful. Greater force is need to complete the cutting of the sample and hold the jaws in place during insertion and removal.

SUMMARY OF THE INVENTION

The present invention provides a biopsy apparatus, in the form of forceps, graspers or other similar devices, for taking a tissue sample having one or two moving jaw sections. When properly used, the movement of the jaws of the forceps is stable and the jaws are unlikely to misalign due to damage or deformation of the device. The instabilities created by the multiple links and linkage assemblies of the prior art is reduced by elimination of many of the linkages and pins. The jaws and the housing may be formed of a generally rigid material, with a central pivot point about which the jaws rotate. Actuation of the jaws is controlled directly with one or a pair of control wires. The present configuration allows only minimal play thereby increasing the accuracy of the alignment of the jaws and decreasing the difficulty of taking a sample, as well as decreasing the risk of damage to the sample taken, the endoscope, and the forceps. This is an important advantage over the prior art, which may allow significant deformation of the linkages causing the jaws to misalign. Further, since many of the linkages, pins and other members are eliminated, the connections may be more robust and therefore be even less vulnerable to deformation while still allowing a smaller overall size for the biopsy forceps.

Many of the prior art devices, due to the many linkages and linkage assemblies require a relatively long housing, which is disadvantageous when performing endoscopic procedures, especially when the path to the tissue sample site is tortuous, convoluted, narrow, or a combination thereof. The longer the rigid portion of the housing, the increased likelihood that the endoscope or the biopsy forceps will be damaged during the procedure or that the user will be unable to properly place the forceps to take the sample. The present invention allows a significantly shorter rigid portion, which is made up of the jaws and a minimal housing. The overall length of the rigid portion in the prior art is frequently more than triple or quadruple the length of the jaws, thereby forming a significant rigid length which must be feed gently through the endoscope's channel.

Further, some prior art devices use significant portions of the internal cavity of the jaws for the actuation mechanism, thereby decreasing the size of the sample taken or increasing the size of the jaws. In the present invention, the jaws of the device are generally unencumbered, so virtually the entire length of the jaws is used for the tissue sample.

Many of the prior art devices also require that additional space be available surrounding the rigid housing during operation of the forceps to allow for the multiple linkages to move beyond the boundary of the rigid housing or sleeve. In the present invention, the only portions of the device which may move out beyond its initial perimeter are the jaws as they open to obtain a sample and the control wire(s) which slide within grooves around the back of the jaws.

In keeping with the foregoing discussion, the present invention takes the form of a jawed endoscopic instrument which has one or two moving jaws. One or two control wires attach to the lower portion of the moving jaws. Each control wire is located within a groove or enclosed channel which passes along the side and preferably to the back of the jaw. The end of the control wire is connected with the jaw so that when the control wire is moved, the force from the wire moved the jaw about its pivot point. If two moving jaws are present, the pivot point is preferably centrally located in the housing. If only a single moving jaw is used, the pivot point may be central, or it may be offset.

BRIEF DESCRIPTION OF THE DRAWINGS

FIG. 6 is a biopsy forceps having round cup jaws.

FIG. 7 is a biopsy forceps having short oval cup jaws.

FIG. 8 is a biopsy forceps having long oval cup jaws.

FIG. 9 is a hot biopsy forceps having long oval cup jaws.

FIG. 10 is a biopsy forceps having long oval cup jaws and a spike.

FIG. 11 is a biopsy forceps having long serrated jaws.

FIG. 12 is a biopsy forceps having long serrated jaws and a spike.

FIG. 13 is a grasping forceps having alligator jaws.

FIG. 14 is a grasping forceps having rat tooth jaws.

DETAILED DESCRIPTION

Figure 1:
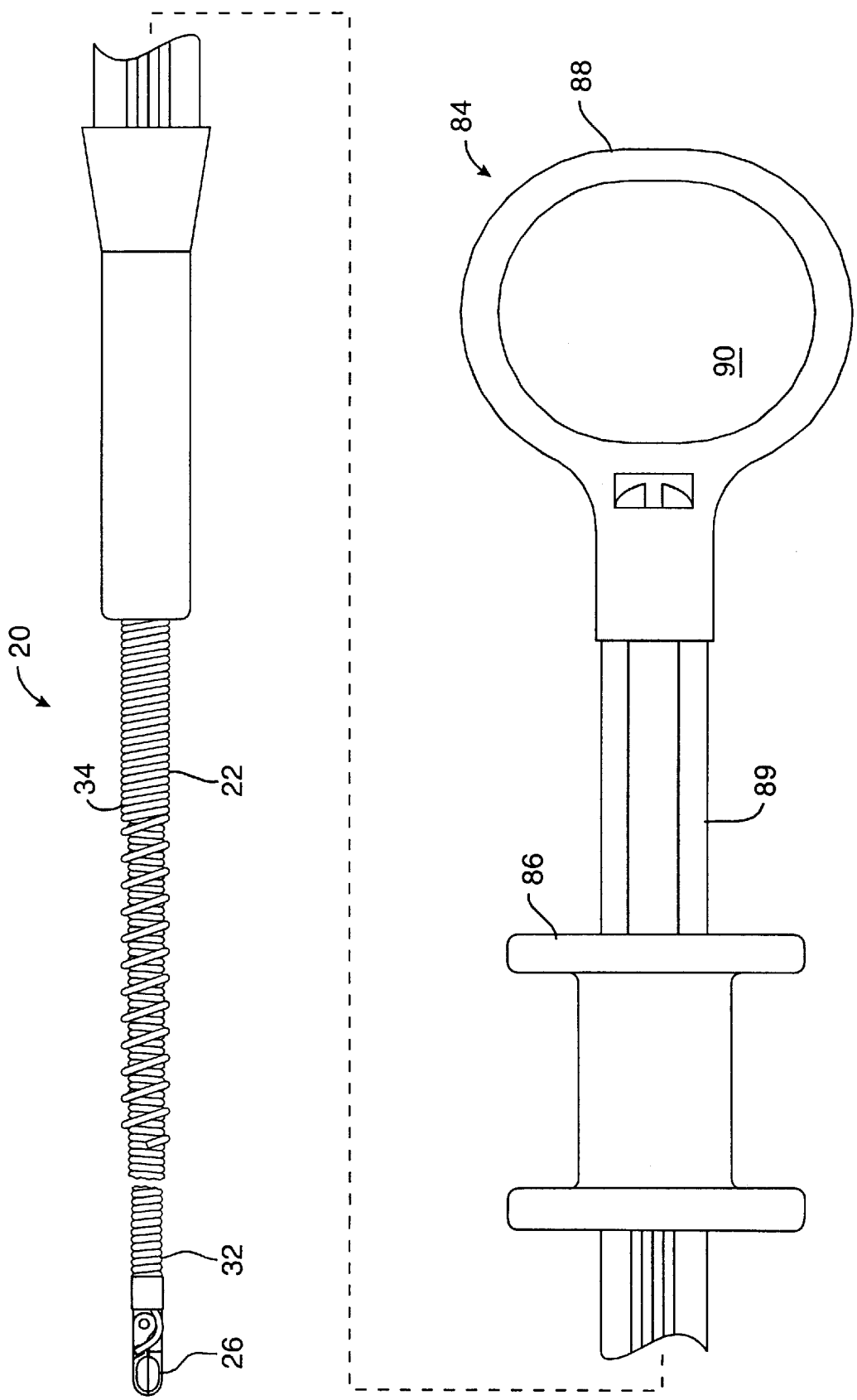
FIG. 1 is a side view of the endoscopic biopsy forceps in the closed position.

Although the present invention may take other forms such as graspers, the device shown in the figures included herein are primarily biopsy forceps 20 for use in endoscopy to take tissue specimens from the body. The biopsy forceps 20 includes a flexible sheath 22, such as a flexible polymeric tubing, coiled steel or the like, having a first end from which control of the forceps 20 is effected by the user. A suitable operating mechanism for actuating the forceps is provided at the first end of the sheath 22 which is connected to one or two control wires 24. The control wire 24 is longitudinally movable within the sheath 22, and the suitable operating mechanism or means will control movement of the control wire 24 therethrough. The device further includes a pair of biopsy jaws 26 connected to a housing 28 which is fixedly attached to the second end of the sheath 22. The biopsy jaws 26 are operatively connected to the control wire 24, which will be more fully described. At least one of the jaws 26 is moveable between open and closed positions with respect to the other of the jaws 26.

Although many other configurations are envisioned, in an exemplary embodiment the sheath 22 would be formed from two welded sections of coil 32, 34. The distal portion of the sheath 22 is preferably more flexible than the proximal portion. The added flexibility may be created by tapering the coil 34 by grinding. The control wire 24 may be a single solid wire, coiled, multi-strand, etc. or other combinations thereof, such as consisting of two or more sections, depending on the requirements or qualities desired. The control wire 24 is preferably formed of two sections. The proximal section is a multi-strand cable, and the distal section is a solid wire.

The length of the forceps 20 will vary greatly depending on the intended use. Standard forceps 20 are currently designed in the range of 20–260 centimeters. However, the present invention may be longer or shorter than this range if desired.

The forceps 20 may also be designed for other uses such as laparoscopic surgery or any other device which requires accurate movement of jaws 26 between 10 open and closed positions, and may therefore be made in a variety of diameters from less than a centimeter to a meter or more depending on the application. As biopsy forceps 20, current standard diameters include a wide range of instrument diameters between 1.0 and 10.0 mm. Bother larger and smaller sizes may be created depending on the needs of the user. The operating mechanism is preferably formed into a handle 84 comfortable for the user to hold and actuate. A sliding trigger 86 may take the form of a spool or two-finger pull which slides along a stem 89. A thumb ring 88 may be formed into or attached to the end of the stem 89. The thumb ring 88 has a hole 90 through which a thumb or finger may rest to aid in moving the sliding trigger 86 by providing opposing pressure. If preferred, a scissor-type, pistol grip or other style handle may also be used.

Figure 2:
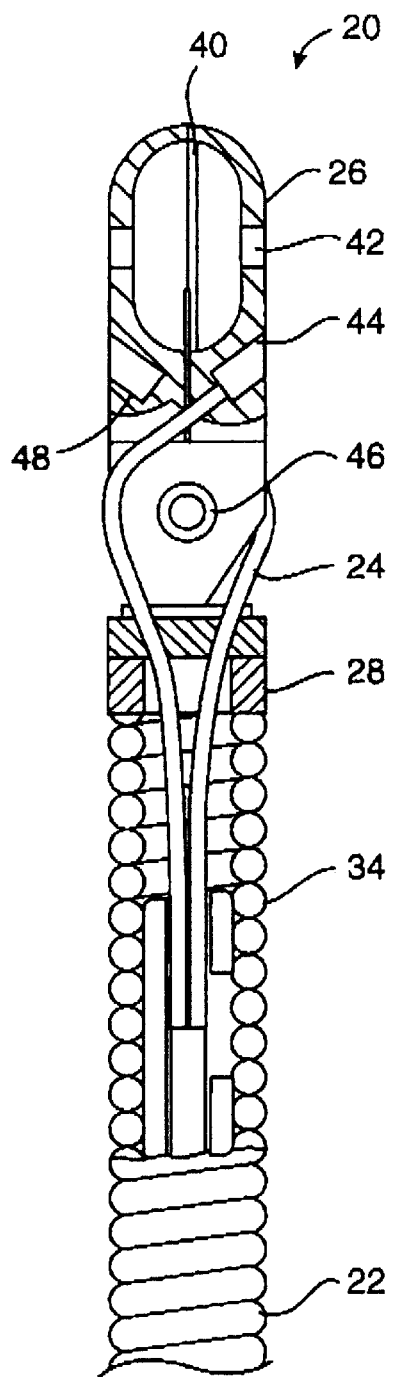
FIG. 2 is a close-up, partial cross-section, side view of the endoscopic biopsy orceps in the closed position.
Figure 3:
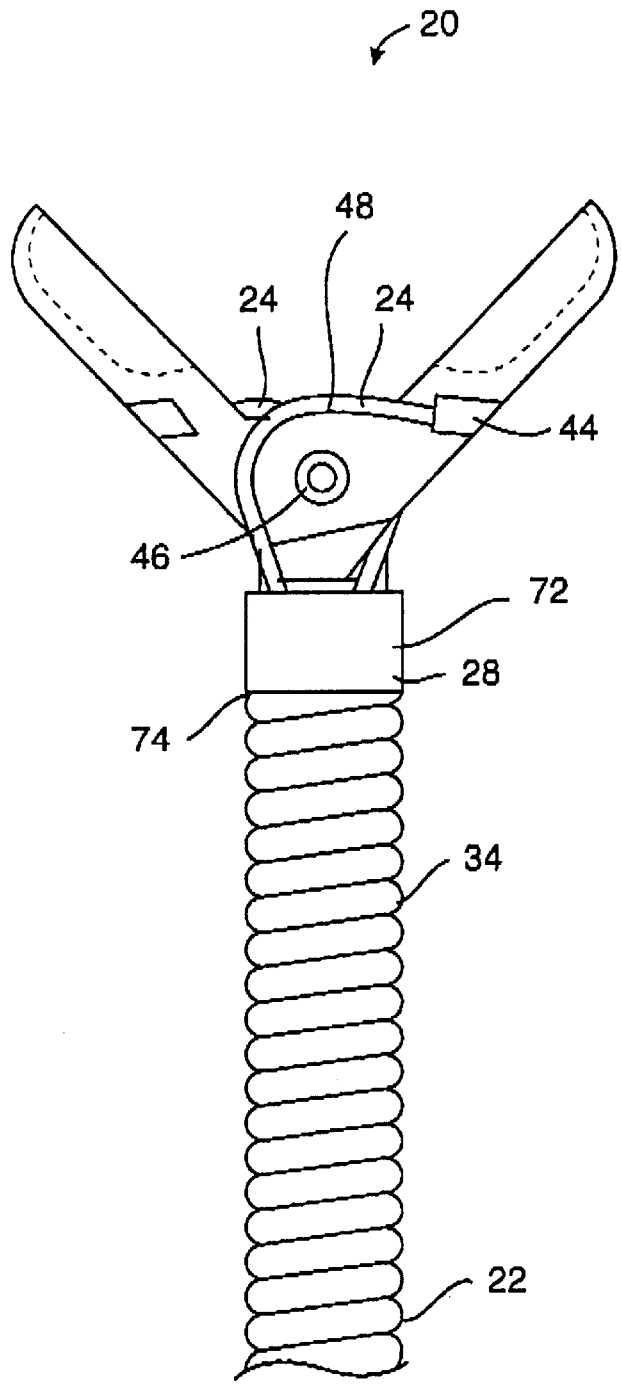
FIG. 3 is a close-up side view of the endoscopic biopsy forceps in the open position.

FIGS. 1–3 show a first embodiment of a biopsy forceps 22 in which two jaws 26 move about a single, central pivot point 46. A pair of control wires 24 extend up through the sheath 22 and run along or through a groove, channel, or passage 44 which extends to and/or around the back side of each of the jaws 26. To provide extra support for the wire 24 and to keep the wire 24 out of contact with other bodies, the channel 44 may be enclosed. The control wires 24 may be two entirely discrete pieces, or they may be connected to assure symmetrical movement of the jaws 26. If the wires 24 are connected, the connection may be a discrete point, or the wires 24 may be woven together along part of their length. The end of the each wire 24 connects to the back, side, or base of each jaw 26. For optimal control of the jaws 26, the ends of the control wires 24 should be attached to the jaws 26 approximately tangential to a circle around the point of rotation. As the angle between the control wire and a line tangential to the circle increases, the amount of force which is translated into the opening and closing motions of the jaws 26 is decreased. However, the control wire 24 may still be connected to the jaws 24 in virtually any configuration, including almost parallel to a line through the point of rotation, while still providing a force to open and close the jaws 26.

The connection 48 of the wire 24 to the jaw 26 may be created by any number of methods, including soldering, welding, crimping, etc. Alternately, the end of the wire 24 may have an end cap or other widened portion which engages a narrow or necked portion of the groove 44. Beyond the end of the wire 24, especially if only an interference connection is used, is a wall against which the end or cap of the wire presses to move the jaws 26 apart.

When a user wants to move the jaws 26 apart, the control wires 24 are pushed, which feeds the distal portions of the wires 24 along the grooves 44 on the back of the jaws 26. The end of the control wires 24 then press against the end walls, if present, or against whatever connection is used. The force applied moves each of the jaws 26 outward, thereby opening the biopsy forceps 20. To close the jaws 26, the user pulls the control wires 24, which draws the wires 24 back through the grooves 44. The end cap pulls against the narrowed portion of the groove or the connection 48, then pulls the jaws 26 towards one another, thereby closing the forceps 20. As may be noted by examination of the drawings, the geometry of the forceps 20 and control wire 24 means that the force which pushes and pulls on the jaws 26 varies as the jaws 26 are moved. When the jaws 26 are closer to the closed position, a greater proportion of the force applied to the control wires 24 is applied to the jaws 26. Since, in general, the most force is needed to make the final cut through the sample in the forceps 20 as they approach the closed position, it is optimal that the greatest proportion of force is available at the point at which it is most needed. Also the present configuration has the greatest decrease in the play in the mechanism while close to and in the closed position which is when it is most important that the jaws 26 meet properly. This is entirely opposite to many of the prior art devices where the least force and the most play are allowed in the closed position.

Figure 4:
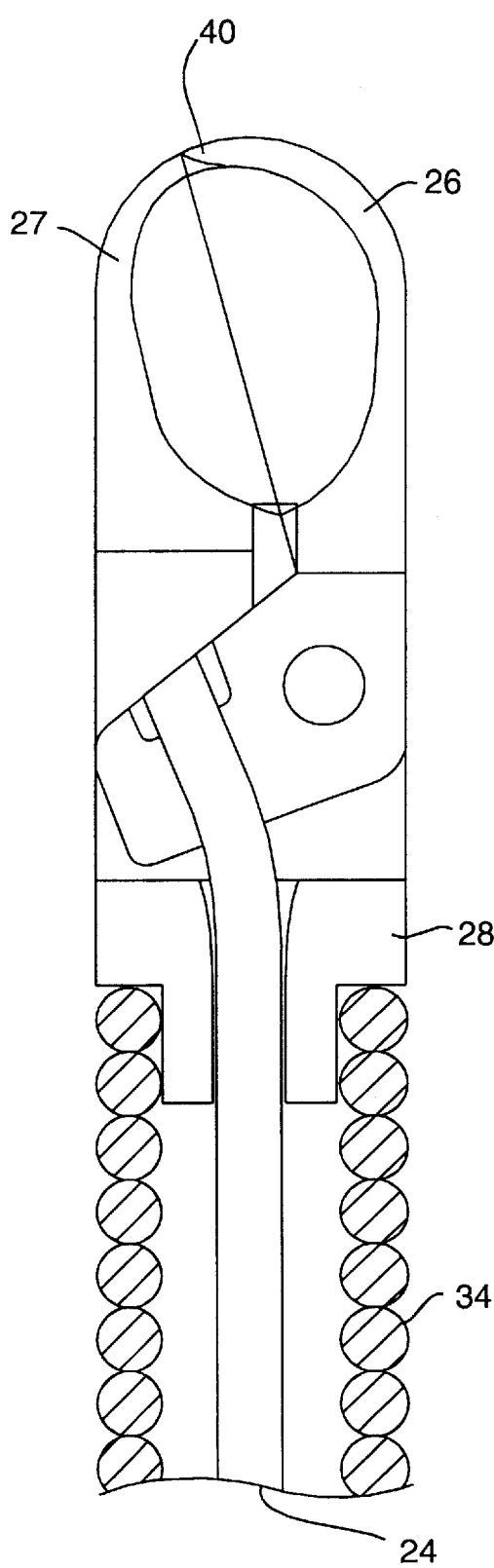
FIG. 4 is a close-up side view of a single moving jaw embodiment of the endoscopic biopsy forceps in the closed position.
Figure 5:
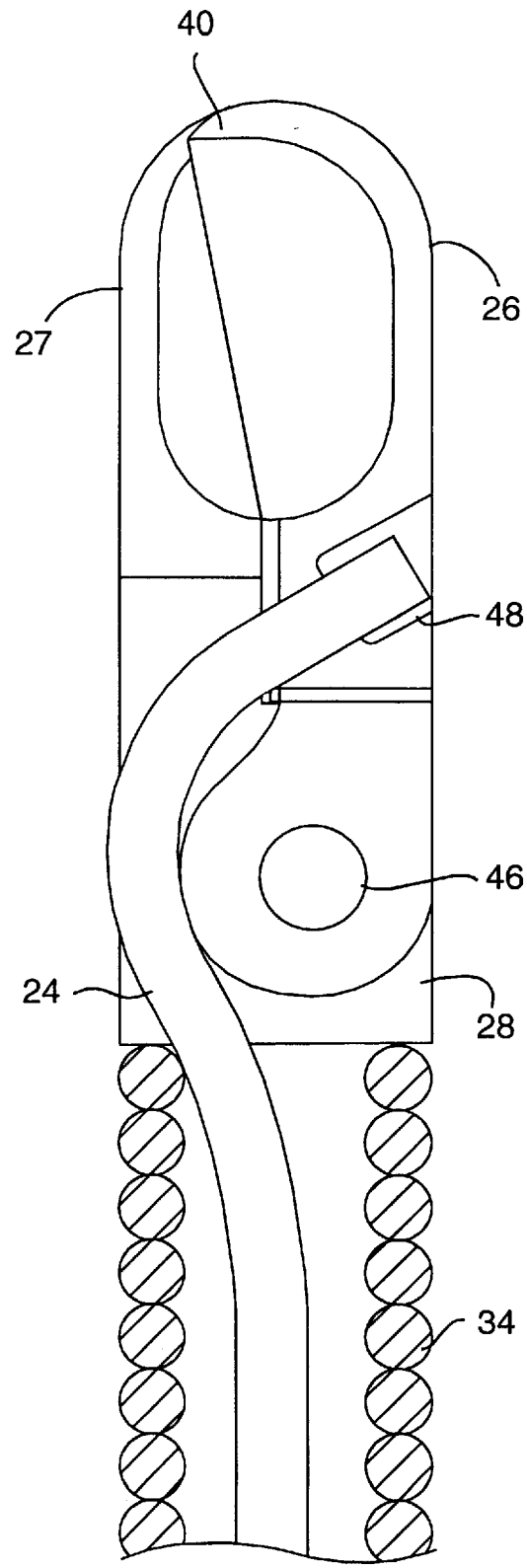
FIG. 5 is a close-up side view of a second single moving jaw embodiment of the endoscopic biopsy forceps in the closed position.

FIGS. 4 and 5 show two embodiments of the biopsy forceps 20, each formed with a single moveable jaw 26. The single control wire 24 is connected to the single moveable jaw 26. The other jaw 27 would be fixedly attached to the housing 28 and would therefore be stationary. The single moving jaw 26 would open and close to facilitate obtaining a sample. For optimal cutting, if only a single cutting edge 40 is used, the cutting edge 40 would preferably be located on the moving jaw 26. When moved into the closed position, the jaws 26, 27 cut through the tissue and meet to remove a tissue sample from an organ and contain the sample during the removal process. An optional hole 42 may extend through the wall of one or both of the jaws 26, 27. The hole 42 allows fluid or other extraneous material to escape the jaws 26 as the jaws 26 close, thereby causing less trauma to the sample being removed from the patient.

In these embodiments, the housing 28 is preferably a generally cylindrical body 72 through which the control wire(s) 24 join to the jaws 26. The base 74 of the housing 28 is connected to the second end of the sheath 22. The connection may be created by soldering, adhesive, crimping, threading, welding or other known connection methods. Although a second pivot point may be used, a single central pivot point 46, about which the jaws 26 rotate, is preferably centrally located within the housing.

The device may optionally include a spike 100 attached within the mouth of the housing. The spike 100 is used to facilitate the taking of tissue samples during use. If preferred, the spike 100 may be barbed to aid in retaining the sample in the forceps 20 while the jaws 26 are closing to cut away the sample.

An alternate embodiment of the invention may have a rigid, semi-rigid, or articulated shaft. Other embodiments may have a malleable shaft, allowing the user to form the shaft into a desired shape prior to insertion into the body. In malleable embodiments, the channel within the sheath 22 which houses the control wire 24 must be of sufficient size to allow the sheath 22 to be in a bent configuration and have sufficient room for the control wire 24 to also be bent and still to move freely in the longitudinal direction. In these embodiments, it is preferable to use a solid control wire or rod 24 to provide additional stability when pushing the control wire 24 to open the jaws 26. Such embodiments would be useful for laparoscopic surgery.

FIGS. 6–14 show several alternate embodiments using the actuation mechanism of the present invention. FIG. 6 is a biopsy forceps having round cup jaws. FIG. 7 is a biopsy forceps having short oval cup jaws. FIG. 8 is a biopsy forceps having long oval cup jaws. FIG. 9 is a hot biopsy forceps having long oval cup jaws and having an electrical connection for cauterization. FIG. 10 is a biopsy forceps having long oval cup jaws and a spike. FIG. 11 is a biopsy forceps having long serrated jaws. FIG. 12 is a biopsy forceps having long serrated jaws and a spike. FIG. 13 is a grasping forceps having alligator jaws. FIG. 14 is a grasping forceps having rat tooth jaws.

The parts of the biopsy forceps 20 may be created by any conventional method including, but not limited to, conventional machining, turning, boring, grinding, electrical discharge machining, casting, molding such as injection, therefrom, etc. or combinations thereof.

Many features have been listed with particular configurations, options, and embodiments. Any one or more of the features described may be added to or combined with any of the other embodiments or other standard devices to create alternate combinations and embodiments.

Although the examples given include many specificities, they are intended as illustrative of only one possible embodiment of the invention. Other embodiments and modifications will, no doubt, occur to those skilled in the art. Thus, the examples given should only be interpreted as illustrations of some of the preferred embodiments of the invention, and the full scope of the invention should be determined by the appended claims and their legal equivalents.

What is claimed is:

1. An endoscopic instrument, comprising:
   a sheath having a proximal end a distal end and a channel extending therethrough, said channel being generally centered within said sheath,
   a housing connected with said distal end of said sheath,
   a handle connected with said proximal end of said sheath,
   a first jaw having a pivot point, said first jaw having an open position and a closed position,
   a channel in said first jaw, said channel passing along a side of said first jaw, a second jaw, and an actuation wire having a proximal end, a distal end and a distal portion, said proximal end of said actuation wire being connected with said handle, said distal end of said actuation wire being connected with said first jaw at a connection point distal to said pivot point, said distal portion of said actuation wire located within said channel in said first jaw, said actuation wire extending through said channel in said sheath, wherein when said actuation wire is moved longitudinally along a body of the instrument, said first jaw moves between the open position and the closed position.

2. The endoscopic instrument of claim 1 wherein said actuation wire is connected to said handle by a core wire passing through said sheath.

3. The endoscopic instrument of claim 1 wherein said actuation wire is attached to an exterior surface of said first jaw.

4. The endoscopic instrument of claim 1 wherein said actuation wire is attached to a back surface of said first jaw.

5. The endoscopic instrument of claim 1 wherein said actuation wire is attached to a side of said first jaw.

6. The endoscopic instrument of claim 1 wherein said second jaw is stationary.

7. The endoscopic instrument of claim 1 wherein said second jaw has a pivot point, an open position, a closed position and a channel passing along a side thereof.

8. The endoscopic instrument of claim 7 wherein said pivot point of said first jaw is coincident with said pivot point of said second jaw.

9. The endoscopic instrument of claim 1 further comprising a spike extending out from said housing.

10. The endoscopic instrument of claim 1 wherein said actuation wire is connected to said first jaw such that, at a point proximal to said connection point, a longitudinal axis of said actuation wire is approximately tangential to a circle with a center at said pivot point.

11. The endoscopic instrument of claim 1 wherein at least a portion of said channel in said first jaw is distal to said pivot point.

12. The endoscopic instrument of claim 1 wherein said connection point is distal to said pivot point when said first jaw is in said open position.

13. The endoscopic instrument of claim 1 wherein said connection point is distal to said pivot point when said first jaw is in said closed position.

14. An endoscopic instrument, comprising:

a sheath having a proximal end and a distal end, a housing connected with said distal end of said sheath, a handle attached to said proximal end of said core wire, a first jaw being pivotable around a pivot point, said first jaw having an open position and a closed position, a first channel in said first jaw, said first channel passing along a side of said first jaw, a second jaw being pivotable around said pivot point, said second jaw having an open position and a closed position, a second channel in said second jaw, said second channel passing along a side of said second jaw, a first actuation wire having a proximal end, a distal end and a distal portion, said proximal end of said first actuation wire being connected with said handle, said distal end of said actuation wire being connected with said first jaw at a connection point distal to said pivot point, said distal portion of said first actuation wire being located within said first channel in said first jaw, and a second actuation wire having a proximal end, a distal end and a distal portion, said proximal end of said second actuation wire being connected with said handle, said distal end of said second actuation wire being connected with said second jaw at a second connection point distal to said pivot point, said distal portion of said second actuation wire being located within said second channel in said second jaw, wherein when said first and second actuation wires are actuated, said first and second jaws move between the open position and the closed position.

15. The endoscopic instrument of claim 14 wherein said first actuation wire and said second actuation wire are connected to said handle by a core wire passing through a majority of said sheath.

16. The endoscopic instrument of claim 14 wherein said first actuation wire is attached to an exterior surface of said first jaw and wherein said second actuation wire is attached to an exterior surface of said second jaw.

17. The endoscopic instrument of claim 14 wherein said first actuation wire is attached to a back surface of said first jaw and wherein said second actuation wire is attached to a back surface of said second jaw.

18. The endoscopic instrument of claim 14 wherein said first actuation wire is attached to a side of said first jaw and wherein said second actuation wire is attached to a side of said second jaw.

19. The endoscopic instrument of claim 14 further comprising a spike extending out from said housing.

20. The endoscopic instrument of claim 14 wherein said channel is enclosed.

21. The endoscopic instrument of claim 14 wherein said first actuation wire is connected to said first jaw such that, at a point proximal to said first connection point, a longitudinal axis of said first actuation wire is approximately tangential to a circle with a center at said pivot point and wherein said second actuation wire is connected to said second jaw such that, a point proximal to said second connection point, a longitudinal axis of said second actuation wire is approximately tangential to a circle with a center at said pivot point.

22. The endoscopic instrument of claim 14 wherein at least a portion of said first channel in said first jaw is distal to said pivot point and said second channel in said second jaw is distal to said pivot point.

23. The endoscopic instrument of claim 14 wherein said first and second connection points are distal to said pivot point when said first and second jaws are in said open position.

24. The endoscopic instrument of claim 14 wherein said first and second connection points are distal to said pivot point when said first and second jaws are in said closed position.

* * * * *